US009859878B2

(12) United States Patent
Lyden et al.

(10) Patent No.: US 9,859,878 B2
(45) Date of Patent: Jan. 2, 2018

(54) CONTROL CIRCUIT FOR USE WITH A SENSOR, AND MEASUREMENT SYSTEM INCLUDING SUCH A CONTROL CIRCUIT

(71) Applicant: Analog Devices Global, Hamilton (BM)

(72) Inventors: Colin G. Lyden, Baltimore (IE); Donal Bourke, Mallow (IE)

(73) Assignee: Analog Devices Global, Hamilton (BM)

( * ) Notice: Subject to any disclaimer, the term of this patent is extended or adjusted under 35 U.S.C. 154(b) by 0 days.

(21) Appl. No.: 14/517,639

(22) Filed: Oct. 17, 2014

(65) Prior Publication Data
US 2016/0112037 A1     Apr. 21, 2016

(51) Int. Cl.
*H03K 5/003*    (2006.01)
*G01N 27/02*    (2006.01)
(Continued)

(52) U.S. Cl.
CPC ........... *H03K 5/003* (2013.01); *G01N 27/028* (2013.01); *G01N 27/3273* (2013.01); *H03H 11/24* (2013.01)

(58) Field of Classification Search
CPC .................................................. H03K 5/003
See application file for complete search history.

(56) References Cited

U.S. PATENT DOCUMENTS 5,889,393 A  3/1999 Wrathall
6,011,431 A  1/2000 Gilbert
(Continued)

FOREIGN PATENT DOCUMENTS

CN        1307398 A     8/2001
CN        1677299 A    10/2005
(Continued)

OTHER PUBLICATIONS

"European Application Serial No. 13185048.9, Response filed Oct. 3, 2014 to European Search Report mailed Mar. 6, 2014", 15 pgs.
(Continued)

*Primary Examiner* — Hai L Nguyen
(74) *Attorney, Agent, or Firm* — Schwegman Lundberg & Woessner, P.A.

(57) ABSTRACT

A control circuit for use with a four terminal sensor, such as a glucose sensor. The Glucose sensor is a volume product and typically its manufacture will want to make it as inexpensively as possible. This may give rise to variable impedances surrounding the active cell of the sensor. Typically the sensor has first and second drive terminals and first and second measurement terminals, so as to help overcome the impedance problem. The control circuit is arranged to drive at least one of the first and second drive terminals with an excitation signal, and control the excitation signal such that a voltage difference between the first and second measurement terminals is within a target range of voltages. To allow the control circuit to work with a variety of measurement cell types the control circuit further comprises voltage level shifters for adjusting a voltage at one or both of the drive terminals, or for adjusting a voltage received from one or both of the measurement terminals.

20 Claims, 10 Drawing Sheets

(51) Int. Cl.
*G01N 27/327* (2006.01)
*H03H 11/24* (2006.01)

(56) References Cited

U.S. PATENT DOCUMENTS

| | | | |
|---|---|---|---|
| 7,023,263 | B2 | 4/2006 | Chang et al. |
| 7,659,753 | B2 | 2/2010 | Chen et al. |
| 7,919,959 | B2 | 4/2011 | Chung et al. |
| 8,659,349 | B1 | 2/2014 | Lyden et al. |
| 9,000,824 | B2 * | 4/2015 | Miyazaki ............... H03K 5/003 327/307 |
| 2004/0021518 | A1 | 2/2004 | Wrathall |
| 2005/0184711 | A1 | 8/2005 | Chen et al. |
| 2010/0066378 | A1 | 3/2010 | Ahmadi et al. |
| 2013/0194034 | A1 | 8/2013 | Giuroiu |

FOREIGN PATENT DOCUMENTS

| | | |
|---|---|---|
| CN | 1818819 A | 8/2006 |
| EP | 1387478 A2 | 2/2004 |
| TW | 588393 B | 5/2004 |

OTHER PUBLICATIONS

"International Application Serial No. PCT/IB2015/002097, International Search Report mailed Apr. 20, 2016", 4 pgs.

"International Application Serial No. PCT/IB2015/002097, Written Opinion mailed Apr. 20, 2016", 5 pgs.

Wen-Yaw Chung et al., "A 600µ W Readout Circuit with Potentiostat for Amperometric Chemical Sensors and Glucose Meter Applications", 2007 IEEE Conference on Electron Devices and Solid-State Circuits, Tainan, Taiwan, Dec. 20-22, 2007, pp. 1087-1090, XP031507806.

Ahmadi M. M. et al., "Current-Mirror-Based Potentiostats for Three-Electrode Amperometric Electrochemical Sensors", IEEE Transactions on Circuits and Systems, I: Regular Papers, IEEE, US, vol. 56, No. 7, Jul. 1, 2009 (Jul. 1, 2009), pp. 1339-1348, XP011333458.

EP Communication with European Search Report issued in EP Application No. 13185048.9, dated Mar. 6, 2014, 10 pages.

TW Office Action issued in TW Appln. No. 102134360, dated Jan. 12, 2015, 13 pages (with EN translation).

* cited by examiner

CONTROL CIRCUIT FOR USE WITH A SENSOR, AND MEASUREMENT SYSTEM INCLUDING SUCH A CONTROL CIRCUIT

RELATED APPLICATION

This application relates to application "Control Circuit for Use With a Four Terminal Sensor, and Measurement System Including Such a Control Circuit," filed on Jan. 17, 2014 as U.S. patent application Ser. No. 14/158,416, which is a Divisional Application of U.S. patent application Ser. No. 13/626,630, filed on Sep. 25, 2012, now issued as U.S. Pat. No. 8,659,349.

FIELD

The present disclosure relates to a control circuit for use with a sensor, where the volt-current characteristics change in response to a measurement; a combination of a sensor and a control circuit; and a method of improving accuracy of a measurement system when used with a sensor. The sensor may, for example, be a biological sensor such as a glucose sensor. The sensor may be a sensor where excitation and measurement terminals are separated from one another. An example of such a sensor is four terminal sensor.

SUMMARY

According to a first aspect of the present disclosure there is provided a control circuit for use with a sensor. The sensor may have first and second drive terminals and first and second measurement terminals, The control circuit is arranged to drive at least one of the first and second drive terminals with an excitation signal, and control the excitation signal such that a voltage difference between the first and second measurement terminals is within a target range of voltages. The control circuit further comprises one or more voltage level shifters for adjusting a voltage at one or both of the drive terminals, or for adjusting a voltage received from one or both of the measurement terminals.

It is thus possible to use the control circuit with a wide range of sensors. The control circuit may include one or more attenuators for attenuating a voltage difference, DC or AC or both, between the first and second measurement terminals. The attenuator(s) may include the level shifting function. Furthermore it is also possible to enable the control circuit to be used with a range of input voltages. This can be advantageous where the control circuit may be used in a range of products. If, for example, the control circuit is to be provided in a glucose sensor then some of the sensor products may be designed for a market where compactness is valued, and hence the battery size or available voltage may be limited in order for product designers to meet a desired size or form for the product. Other versions of the product may be designed to be used in less fashion conscious markets, but where a long time between battery changes or cost is a dominant factor. In these circumstances a product may be designed to work with bulkier and less expensive batteries. This may mean that for this item of equipment the voltage supplied by the battery or batteries may be different. The control circuit may have been optimized to work with a relatively low voltage, say around 1V, in order to maximize operational life or to work with a given battery type. For example NiCd and NiMH batteries produce about 1.2V per cell, Lithium-ion batteries are about 3.6V per cell, whereas Alkaline batteries have a terminal voltage that can range from 1.6V to 1V depending on how discharged they are.

Whilst in absolute terms these variations are only fractions of a volt, in percentage terms they are large changes and can significantly affect the internal voltages of a control circuit.

Advantageously a driver circuit may be provided, and may have a supply voltage different to that provided to other parts of the control circuit. This can be of use in reducing power consumption when the circuit is battery powered.

Advantageously the control circuit has first and second reference voltage input terminals for accepting a differential reference voltage. The differential reference voltage sets the target voltage for the voltage difference between the first and second measurement terminals.

The sensor may comprise two, three, four or more terminals. For sensors having two or three terminals then two or one, respectively, of the drive terminals and measurement terminals are shared at a physical node. Preferably the sensor is a four terminal sensor.

Advantageously the four terminal sensor comprises a load whose impedance varies, amongst other things, as a function of concentration of a chemical, enzyme, or biological material. Alternatively the impedance of a load may vary as a function of a reaction. It is known that sensors for electrical detection of biological parameters can be produced. Examples of such electrically readable biological sensors in widespread use include blood glucose measurement strips that are used in the care of diabetes.

According to a second aspect of the present disclosure there is provided a control circuit constituting an embodiment of the first aspect of the invention in combination with a four terminal sensor.

DESCRIPTION OF THE FIGURES

Embodiments of this disclosure will now be described, by way of non-limiting example, with reference to the accompanying Figures, in which.

DESCRIPTION OF EXAMPLE EMBODIMENTS

Figure 1:
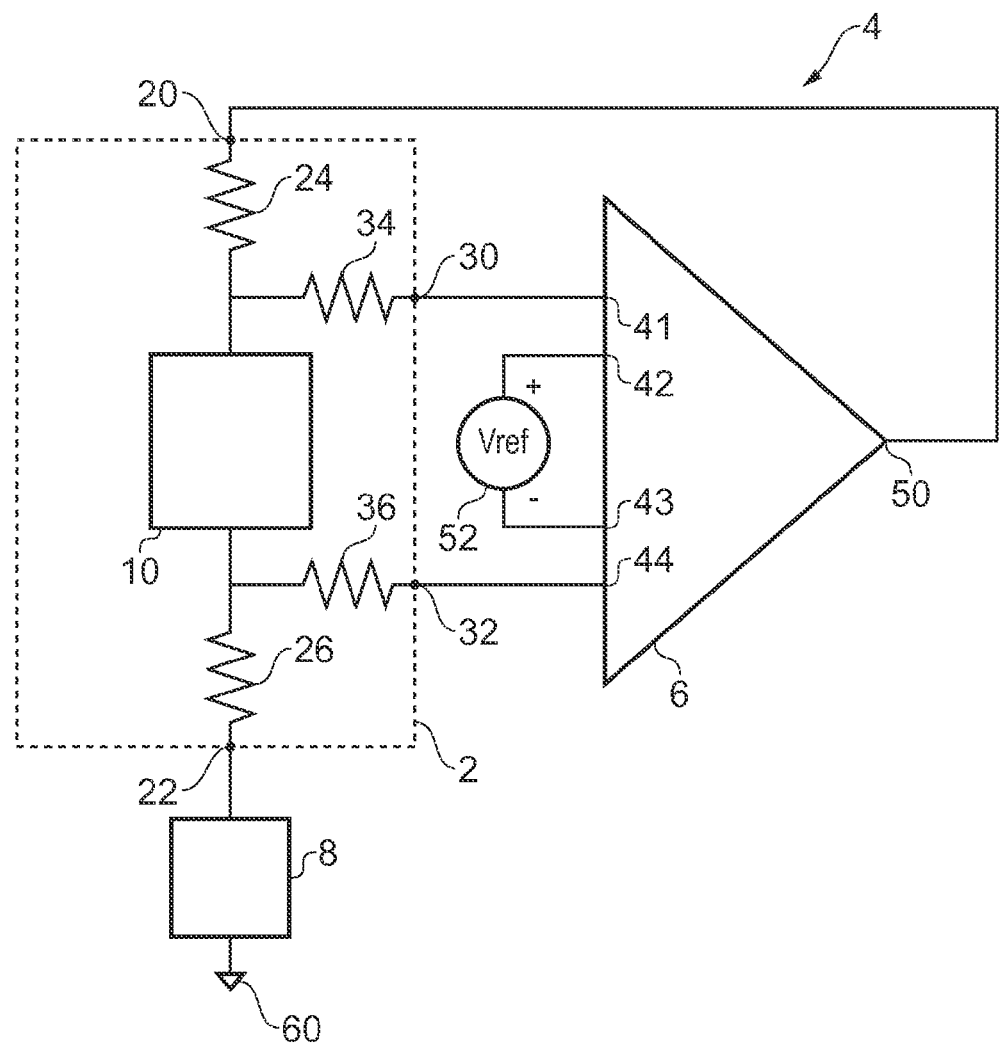
FIG. 1 is a circuit diagram of a known measurement circuit.

FIG. 1 is a circuit diagram of a measurement circuit comprised of a four terminal sensor, generally designated 2, in combination with a control circuit, designated 4, and a current measurement circuit designated 8. Such an arrangement is described in U.S. Pat. No. 8,659,349. The four terminal sensor 2 comprises a load 10 whose impedance varies as a function of a measurand. Thus, for example, the load 10 may be a cell for biological measurement whose impedance varies as a function of an analyte concentration. The analyte may, for example, be blood glucose. The cell may be attached to a substrate and connected to terminals on the substrate such that the cell 10 can be electrically excited and the current flow through the cell monitored. As part of this measurement it is desired to know, with significant accuracy, the voltage across the cell 10 as well as the current through it. However connections to and from the cell 10 may be subject to manufacturing variation and may exhibit impedance, and indeed changes in impedance, which would effect the accuracy of the voltage measurement. In order to overcome such impedance issues, the cell is provided as part of a four terminal sensor. The four terminal sensor comprises a first drive terminal 20, notionally connected to one end of the cell, and a second drive terminal 22 notionally connected to an opposing end of the cell. An impedance, represented by resistor 24 may exist between the first drive terminal 20 and the first end of the cell 10. This first impedance 24 may be deliberate or it may simply be a function of the properties of the cell 10 and the connections made to it and hence may be regarded as being a parasitic component. Similarly a second resistance 26 may exist in the path between the second side of the cell 10 and the second drive terminal 22. The four terminal sensor overcomes the problem of these resistances 24 and 26 by having first and second measurement terminals 30 and 32 connected to the first and second ends of the cell 10, respectively. These connections may also exhibit deliberate or parasitic impedance as represented by resistors 34 and 36, respectively. Although the word "terminal" has been used here, it is to be understood that it can be replaced by the term "node".

The cell output voltages occurring at the first and second measurement terminals 30 and 32 will accurately represent the voltage difference across the cell 10 if no current, or substantially no current, is taken by a measurement circuit connected to those first and second measurement terminals 30 and 32. This condition can, to all intents and purposes be achieved by operational amplifiers employing high impedance front ends. Such high impedance front ends typically use insulated gate field effect transistors as input devices. As a consequence such circuits draw substantially no current from the measurement terminals.

The control circuit 6 in U.S. Pat. No. 8,659,349 was schematically represented as an operational amplifier. This is substantially correct, because although it has first to fourth inputs 41 to 44 its action within the closed loop shown in FIG. 1 is to drive the voltage at its output node 50 so as to minimize the sum of the voltage difference between the voltage occurring at input 41 with respect to the voltage occurring at input 42 and the voltage difference between the signal occurring at signal input 44 with respect to the signal occurring at reference voltage input 43. Each of these differences can be formed by operational amplifiers i.e. the difference between the signals at inputs 41 and 42, and the difference between the signals at inputs 43 and 44, and then each of these differences can act as inputs to a further operational amplifier.

In order for the voltage across the cell 10 to be controlled, current must flow through the cell, for example from the first drive terminal 20 to the second drive terminal 22. As part of the measurement of the biological material to which the cell is responsive, it is necessary to know the magnitude of the current passing through the cell. To this end, a current measurement circuit 8 is provided. In the example shown in FIG. 1 the measurement circuit 8 has been positioned between the second drive terminal 22 and a small signal ground 60. However the current measurement circuit 8 could also be provided in the feedback loop between the output node 50 of the control circuit 6 and the first driven node 20 of the four terminal sensor 2. The person skilled in the art is free to make this choice depending, to some extent, on what current measuring technology or circuit he finds most convenient to implement.

The voltage reference 52 may be arranged to generate a DC voltage pulse, in which case it is desirable to measure the evolution of current with respect to time. However, for checking and calibration purposes it may also be desirable for the voltage reference 52 to generate a changing signal, for example an alternating sinusoid, and in which case it becomes desirable for the measurement circuit 8 to have knowledge of the phase of the sinusoidal signal such that a magnitude and phase change of the current flow may be measured, for example to deduce a complex impedance of the cell 10. The complex impedance may be determined by comparing the magnitude and phase of the voltage difference between the first and second measurement terminals with the magnitude and phase of current flow through the sensor.

It therefore follows that it is also possible to generate an excitation signal in an open loop mode, and measure the resulting currents and voltages.

Figure 2:
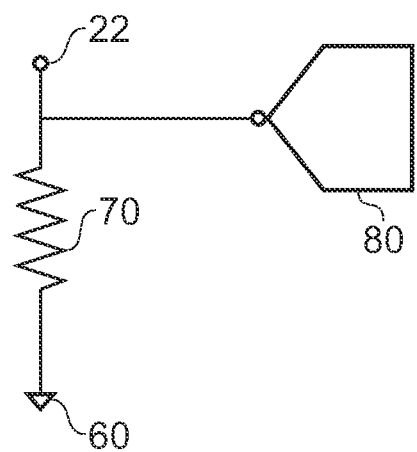
FIG. 2 is a circuit diagram of a known current measurement circuit.

FIG. 2 schematically illustrates a first current measurement circuit which comprises a sense resistor 70 disposed in series between the second driven node 22 and the small signal ground 60. The voltage occurring across the resistor 70 can be measured by an analog to digital converter 80. The analog to digital converter 80 may be implemented in any suitable converter technology, such as sigma-delta, successive approximation or flash technologies depending on the speed and accuracy requirements required by the circuit designer.

Figure 3:
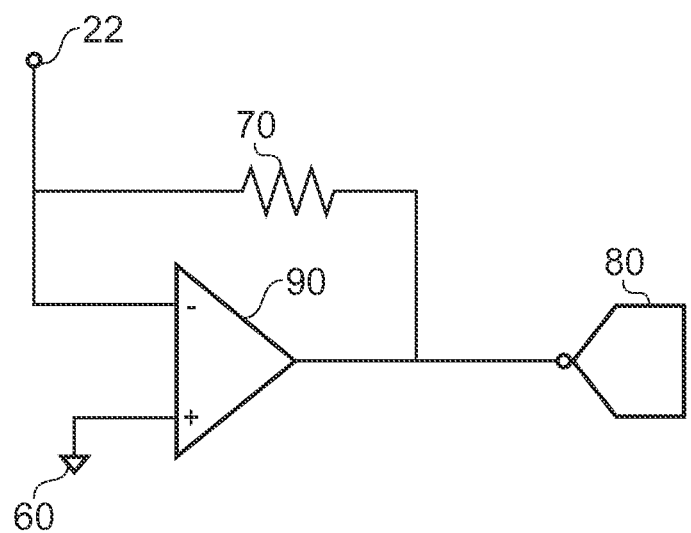
FIG. 3 is a circuit diagram of a further known current measurement circuit.

FIG. 3 shows a variation on FIG. 2 in which the current sense resistor is placed in the feedback loop of an operational amplifier 90 having its inverting input connected to the second drive terminal 22 and its non-inverting input connected to the small signal ground 60. This configuration may be advantageous as it means that the voltage at the second drive terminal 22 is held substantially constant by virtue of the amplifier 90 forming a virtual earth, and the impedance of the resistor 70 may be selected so as to give a greater output voltage range at the output of the amplifier 90. Once again, the output voltage can be digitized by an analog to digital converter 80.

Figure 4:
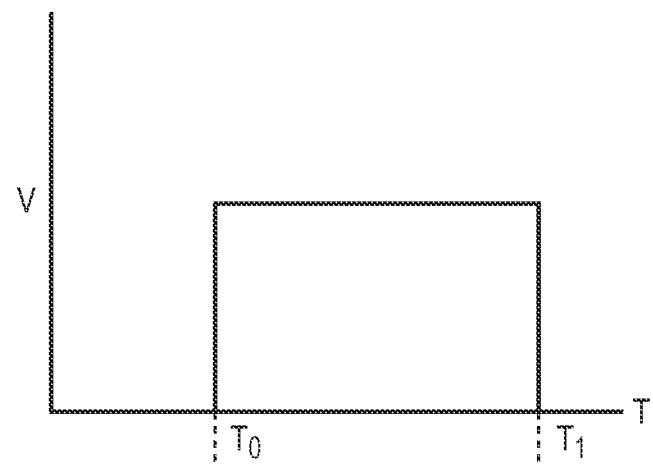
FIG. 4 is a graph representing an excitation signal that may be applied in electrochemical analysis to a suitable measurement cell.
Figure 5:
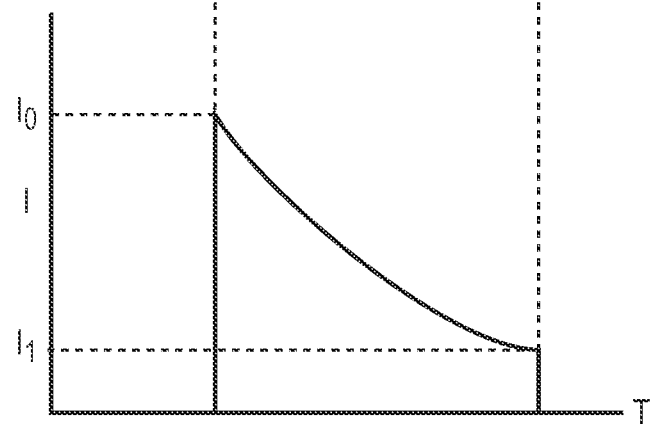
FIG. 5 is a graph of the idealized evolution of current with respect to time for an electrochemical glucose measurement cell.

The load 10 may, for example, be an electronically measured electrochemical strip, of which a glucose strip is a common example. An amperometric measurement protocol for such a strip is illustrated in FIG. 4. During the amperometric measurement, a DC voltage is applied across the strip at time $T_0$ and held constant until time $T_1$. The difference between time $T_1$ and $T_0$ is substantially 1 second and the magnitude of the voltage may be around 500 mV. During the measurement protocol the current across the cell varies substantially as shown in FIG. 5. Thus the current quickly rises to an initial value $I_0$ and decays to a value $I_1$.

The curved shape is a cottrellian curve (it follows a Cottrell equation) whose shape varies substantially as $$\frac{K}{\sqrt{T}}.$$

The value of the parameter K varies as a function of analyte concentration. However, the value of K may also vary as a function of other parameters, a common one being temperature, but it may also vary in the presence of contaminants. In a more complex form of the Cottrell equation, the value of K varies as the square root of a diffusion coefficient for a species being measured, and it is the diffusion coefficient which is a function of temperature It is therefore desirable to make some correction measurements, either before or after the main test, to deduce factors which may be used to modify the value of K, such that, for example, a glucose test becomes more accurate.

Figure 6:
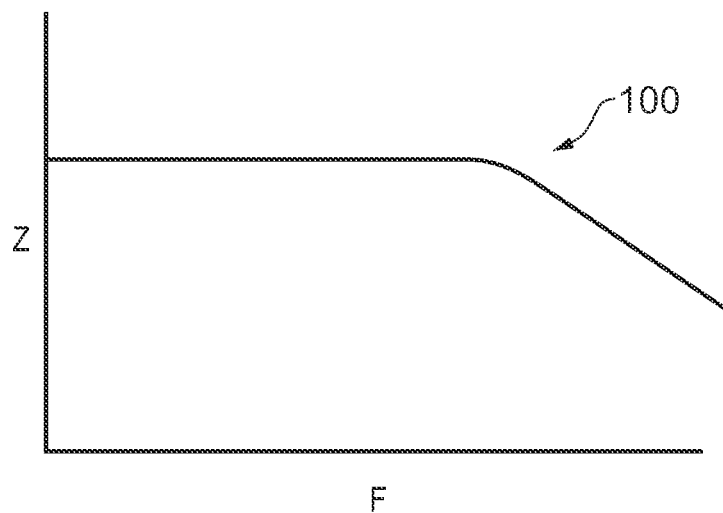
FIG. 6 is a graph of impedance versus frequency for a blood glucose test sensor.

It has been observed by workers in the field that some of these error sources, such as temperature and some interfering chemicals can be deduced by measuring the complex impedance of the cell 10. Thus, for example, it has been observed for a glucose measurement cell that the variation of impedance with respect to frequency as shown in FIG. 6, has a turning point generally indicated 100. The position of the turning point can, as known to the person skilled in the art, be used to derive a correction factor, for example, for measurement of temperature. Thus measuring the impedance as a function of frequency enables the temperature of the cell 10 to be deduced. It is expected that this approach can be extended to many biological sensors responsive to respective analytes.

U.S. Pat. No. 8,659,349 discloses modifications to the control circuit that enable it to use a higher gain in the operational amplifier to achieve greater accuracy whilst maintaining stability of a feedback loop.

Figure 7:
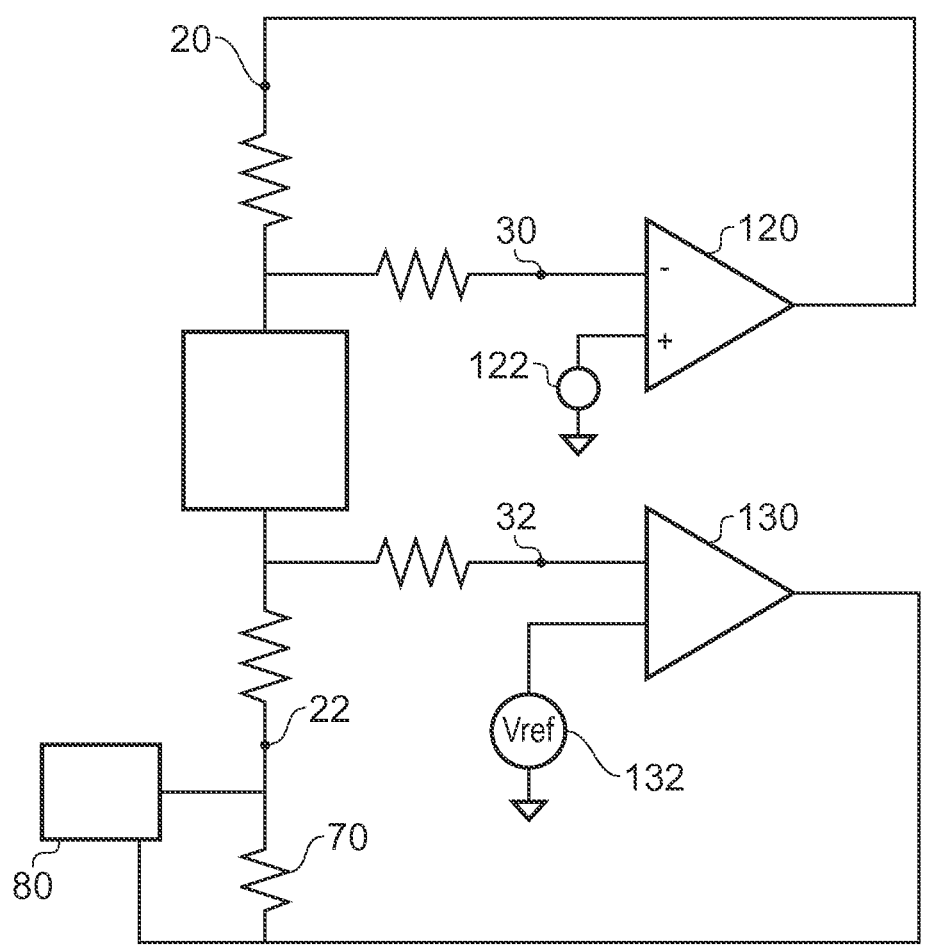
FIG. 7 is a schematic diagram of a further embodiment of a measurement circuit.

For completeness, FIG. 7 illustrates a variation of the circuit shown in FIG. 1 where two control circuits are provided. An upper control circuit 120 receives a first reference voltage from a first reference voltage generator 122 and controls the voltage at the first measurement terminal 30 to match that reference voltage provided by the first reference voltage generator 122. A second control circuit 130 receives a second reference voltage from a second reference voltage generator 132 and controls the voltage at the second measurement terminal 32 to be equal to the voltage from the second reference voltage generator 132. Thus upper and lower limbs of the sensor are driven to respective voltages in a dual ended manner. A current measuring resistor 70 may be inserted in either of the control loops (as by definition the current must be the same in each control loop) and the voltage occurring across the resistor 70 can be digitized by a differential input analog to digital converter 80.

In use, there may be competitive or commercial price pressure on the manufacture of the sensor 10. This may result in modifications to the sensor or the sensor manufacturing process that lead to variations in the cell impedance, as designated by the resistors 24, 26, 34 and 36 in FIG. 1. Lowering of the resistance is, in general, not a problem as the cell 10 would more closely approximate an ideal cell. However, it is more likely that if sensor cells 10 are manufactured for less cost, then the impedances and/or variability of the impedances will increase. For businesses manufacturing large numbers of glucose monitoring cells very modest reductions in manufacturing costs may generate large additional revenues.

Higher impedances may require the use of larger drive signals to set to voltage across the cell 10 to a desired value. However, the increased impedance 26 may also cause the voltage to be offset during operation such that it may no longer fall in a desired input range for the processing circuitry, such as operational amplifiers processing the voltages at the cell's output terminals. This can occur when measuring the cell's response to an analyte or sample, and when calibrating or correcting the result by measuring the complex impedance of the cell 10.

Typically a device such as a Glucose monitor (or other monitor) may be provided as a portable monitor. Consumers want such devices to be compact, light and to have a long battery life. Increasing battery life is often associated with reducing operating voltages within circuit, whereas dealing with measurement cells having larger impedances or more variable impedances generally requires increased operating voltage. It is therefore desirable to provide circuits that can reliably process outputs from sensors having increased internal resistance or other parasitic impendences.

In variations of monitoring circuits, the power supply voltage headroom at the control circuit 6 may be reduced. This may result from increased sensor impedence moving the voltages from the cell closer to one of the supply rails. Increased impedance within a sensor may manifest itself in different ways. If, for example, in some future manufacturing process the value of second resistance becomes increased compared to the other resistors, then the voltages at nodes 30 and 32 both drift upwardly, and this may take the voltages at the inputs 41 and 44 out of a regime where the control circuit delivers its best performance as regards input related offset or linearity. Similarly an increase in the resistance of the first resistor 24 compared to the second resistor 26 would tend to push the voltages at the nodes 30 and 32 towards ground in an open loop system, or require greater drive voltage to node 20.

In an arrangement where the voltage at the nodes 30 and 32 is controlled by a feedback loop, then any increase in resistors 24 and 26 increases the drive voltage that needs to be applied to the first drive terminal 20 compared to the second drive terminal 22. If the sensor 2 is driven with a fixed or predetermined voltage profile then the increase in resistance acts to attenuate the signals as reduced current is provided to the cell. This may be acceptable with some designs of cells but not for others. The control circuit may include differential input stages (such as longtail pairs) driven by current mirrors and consequently the control circuit will work best when the input voltage is not so close to the supply rails that processing the input voltage seeks to reduce voltage headroom requirements of current mirrors or active loads within the control circuit 6 to such an extent that they cease to work properly. This in turn may mean that in battery powered equipment the control circuit 6, 120, 130 may have a relatively narrow range of input voltages where it works properly, and variable or increased cell impedances 24 and 26 may take the voltages at nodes 30 and 32 outside of the ideal operating range for the control circuit 6, 120 or 130. For example, the input stages for signals 43 and 44 may have been tailored by the circuit designer to be centered about an expected input range for signal 32, which might be quite close to the 0V value, whereas the circuit associated with the inputs 41 and 42 may have been designed to be centered around a different, higher voltage, or at least to cope with a higher peak value.

Figure 8:
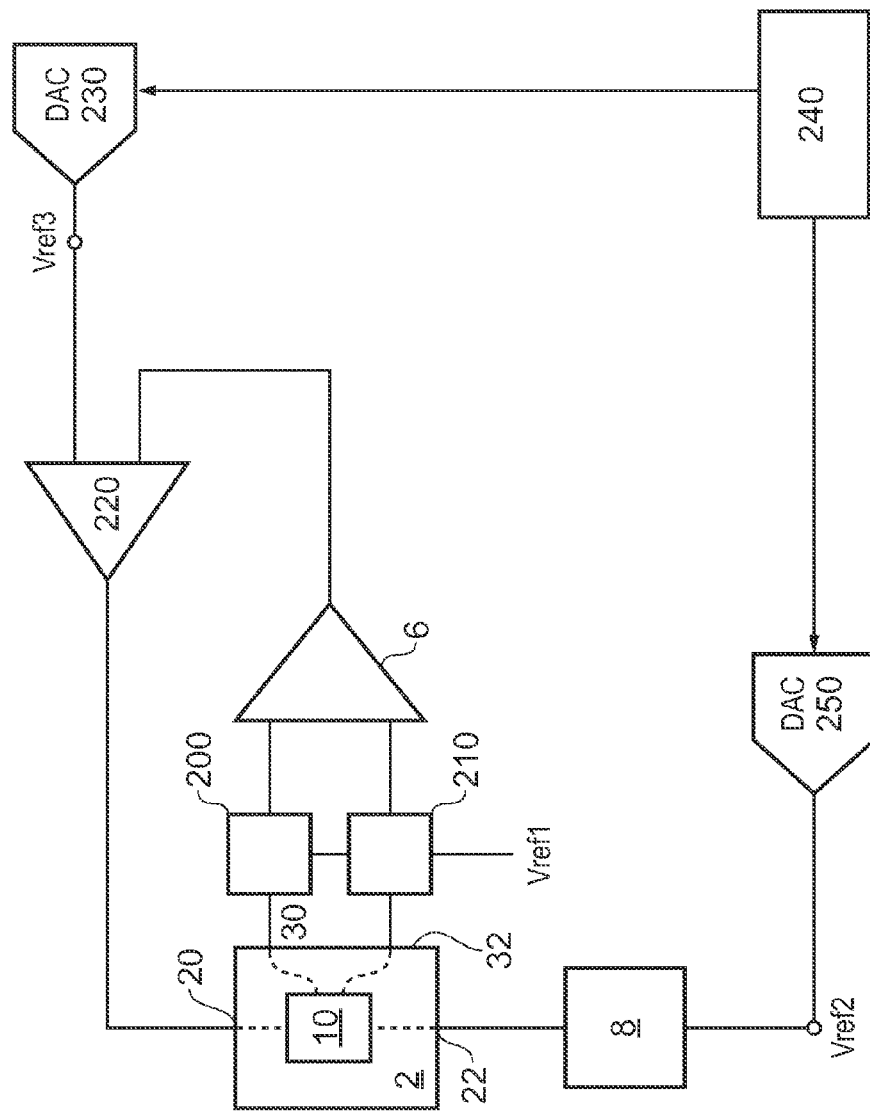
FIG. 8 is a schematic diagram of a further embodiment in accordance with the teachings of this disclosure.

FIG. 8 shows a modification to the arrangement of FIG. 1. In broad terms first and second attenuators, buffers or gain stages 200 and 210 are interposed between the first and second output nodes 30 and 32, and the remainder of the controller 6. Furthermore the attenuators, buffers or gain stages can be referenced to a first reference voltage Vref1 to provide a level shifting operation. The first reference voltage Vref1 may be set to substantially the midpoint of the input voltage range of the controller 6. In can be seen that a variable gain amplifier may allow a gain greater than, equal to, or less than unity to be provided. For simplicity, it will be assumed that attenuators are provided.

Thus if the voltage at the first output 30 is V30 and the voltage of the second output is V32, the first attenuator forms an output voltage $$VA1=(V30-Vref1)a1$$

where a1 is an attenuator factor.

The second attenuator works in the same way such that $$VA2=(V32-Vref1)a1$$

The attenuation factor a1 may be fixed, or may be variable. For example a plurality of resistors may be associated with electrically (or mechanically) controlled switches to set the attenuation factor to a desired value for proper operation of the circuit 6.

Similarly a second reference voltage Vref2 may be variable, such that the current measuring circuit can function correctly and/or to shift the voltages at outputs 30 and 32 of the four terminal sensor 2.

In use, it may also be desirable to add a DC offset such that all the voltages in the circuit have the same polarity with respect to a local reference (such as the −ve terminal of a battery powering the electronic circuit) even though an AC signal is applied to the cell 10 within the sensor 2 to measure the complex impedance of the cell 10.

This can be done by providing a separate driver circuit 220 to drive the first drive terminal 20 of the sensor 2. The driver circuit 220 can be operated at a different voltage range than the rest of the controller 6 so as to be able to drive sensors 2 having larger impedances.

The power supply to the driver circuit 220 may, if necessary or desirable, be formed by a DC to DC boost converter so as to increase the supply voltage from a battery. Inductor based step up converters and capacitor based charge pumps for generating increased voltages are known to the person skilled in the art. Alternatively, the driver circuit may be powered from a battery voltage and other parts of the circuit may receive a reduced voltage from a step down converter, or all parts of the circuit may receive the same supply voltage but each part can be designed or optimized to carry out a specific task. The DC offset may be added to an alternating voltage from the controller 6 by the driver circuit 220. The DC offset may be represented as Vref3 which may be fixed or may be variable, for example, Vref3 may be provided by a DAC 230 in response to a control word from a system controller 240. Vref3 may be subjected to a gain. Similarly Vref2 may be provided by a DAC 342 responsive to the system controller 350 as may Vref1 by its own DAC (not shown). The controller 240 may also monitor the output voltages at one or both of the attenuators 200 and 210 so as to adjust the reference voltages Vref1 and/or Vref2 and/or Vref3 to optimize the performance of the controller 6. Similarly the system controller may also vary the attenuator factor a1 of the attenuators 200 and 210.

Figure 9:
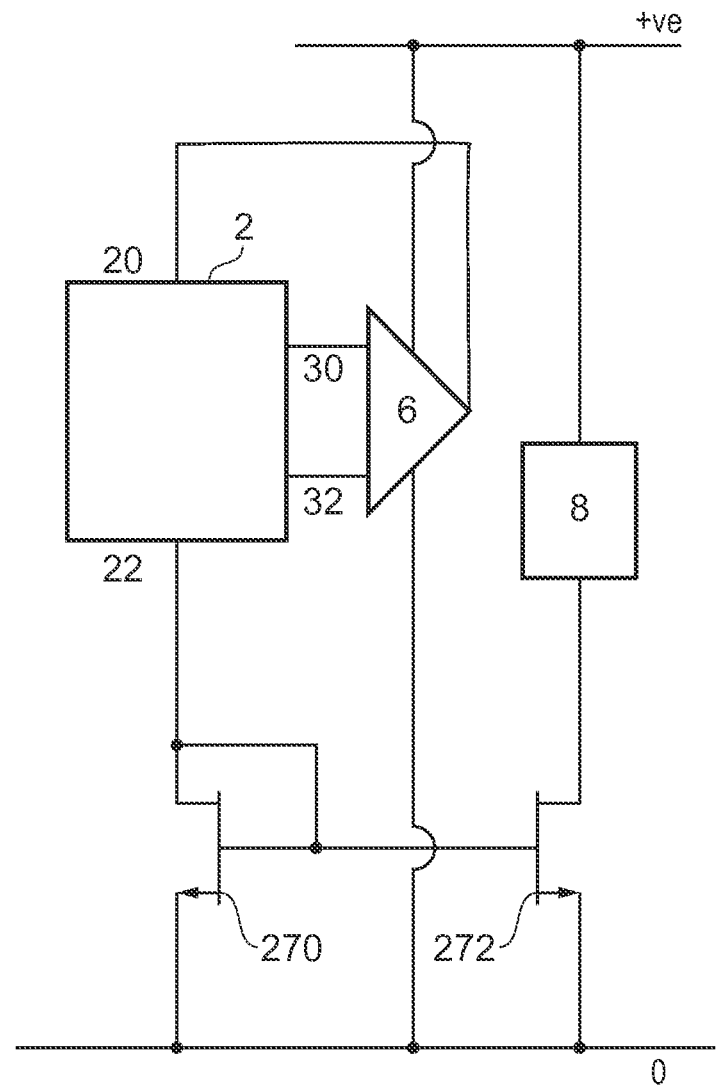
FIG. 9 shows a variation for interconnecting the measurement cell and the current measurement circuit.

The cell 10 and the current measuring circuit 8 have hitherto been described as being in current flow communication by way of a series connection. This need not be the case, as the current flow through the cell could be conveyed to the current measuring circuit by way of a current mirror, as schematically illustrated in FIG. 9. The current mirror formed by transistors 270 and 272 reduces the headroom requirement further by allowing the current measurement circuit to be placed between the supply rails. The transistors 270 and 272 have been illustrated as FETs but could be bipolar transistors. Similarly the current flowing in the output stage of the driver could be mirrored by a current mirror.

Figure 10:
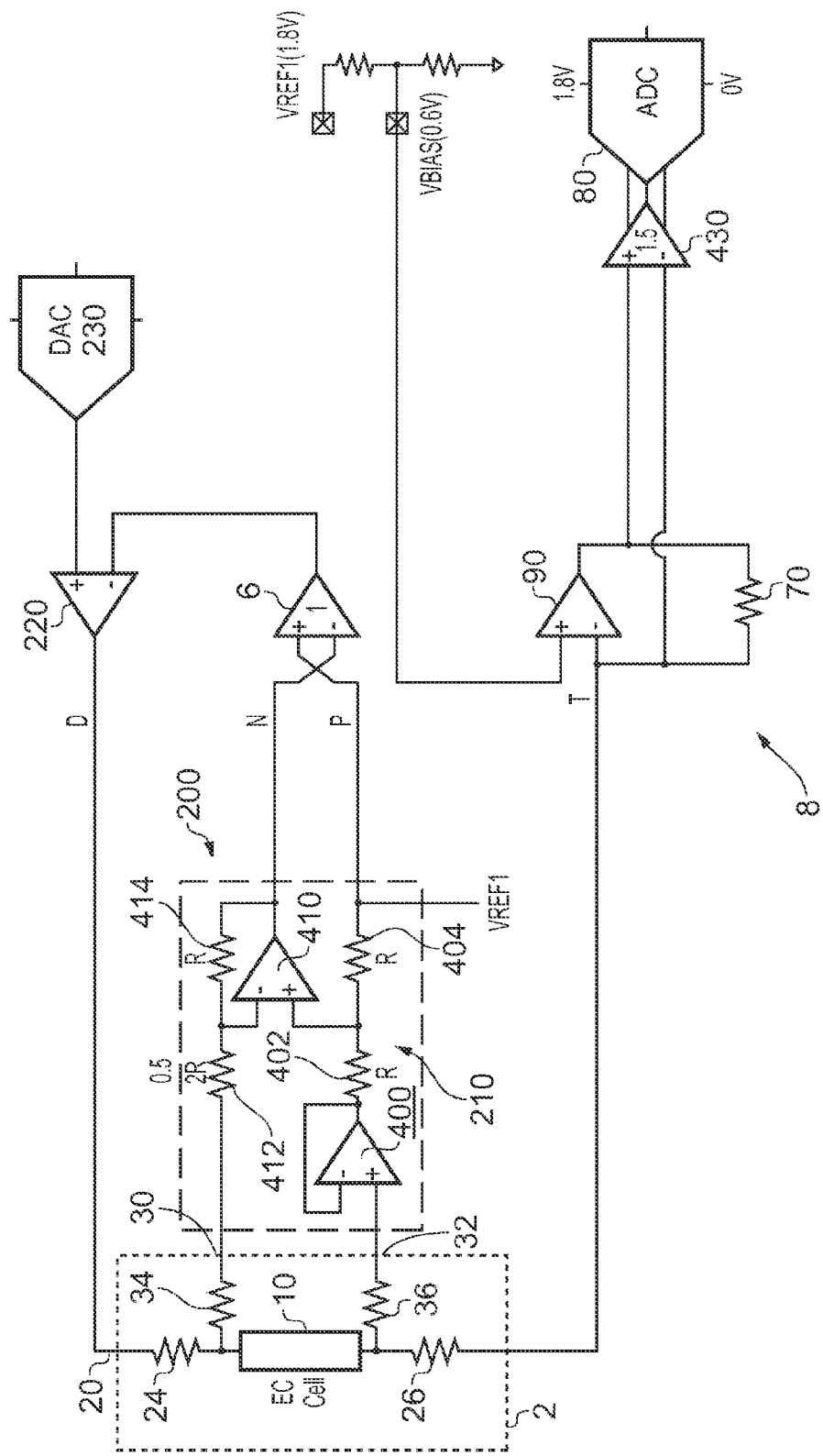
FIG. 10 is a schematic diagram of a further embodiment including means for maintaining an input to the controller within a working input range.

FIG. 10 shows an example of an implementation of the circuit of FIG. 8, and using a current measuring circuit as described with respect to FIG. 3. However, the attenuators 200 and 210 have been implemented in a slightly different way, and one of the inputs of the controller 6 is now tied to Vref1.

The first and second attenuators are now coupled. The voltage from the second output node 32 is provided to a differential amplifier 400 acting as a buffer and voltage follower. The second output node is connected to a non-inverting input of the differential amplifier 400, and an output of the amplifier is connected to the inverting input of the amplifier 400. Two resistors 402 and 404 are connected in series between the output of the amplifier 400 and Vref1. The resistors 402 and 404 form a potential divider, such that the voltage at a node between the resistors, and which is connected to a non-inverting input of a second differential amplifier 410 is $$V = (V32 - Vref1)\frac{R404}{R402 + R404}$$

where R402 is the value of the resistor 402, R404 is the value of the resistor 404 and V32 is the voltage at the second output 32 of the sensor 2. If R402=R404, then the signal voltage is attenuated to one half of its original value. If R402 and R404 are very large then the amplifier 400 may be omitted.

The first output 30 of the sensor could also be provided to a buffer, and the output of the buffer could be provided to an attenuator and level shifter built around a further differential amplifier. However assuming that internal resistance R34 is very small compared to resistor 412, it is also possible to avoid forming a second buffer, as shown in FIG. 10. The output 30 is connected to an inverting input of the amplifier 410 by way of a resistor 412. A feedback resistor 414 is connected between the output 30 and the inverting input. This forms an inverting amplifier with a gain of −R414/R412. Therefore if resistor 412 is twice the size of resistor 414 then a gain of 0.5 will be achieved, thereby matching the attenuation provided by resistors 402 and 404. If resistors 412 and 414 are large compared to the internal resistance 34 then little gain or attenuation error should occur. However, even if this is not the case, the circuit will still function adequately.

It can also be seen that, in the absence of a buffer, some current will flow in the internal resistor 24 to the virtual earth formed at the inverting terminal of the amplifier 410.

However this current is provided by the drive circuit and does not substantially impact on the estimate of the current in the cell 10 as the resistor 34 is arranged to receive the nominal voltage at the 'high side' of the cell 10.

An output of the second amplifier 410 is provided to a first input of the controller 6. The controller 6 may include a 'chopping amplifier' configuration as is known to the person skilled in the art. A second input of the controller is tied to $V_{REF1}$.

As shown in FIG. 10, the current measurement can be performed by a transimpedance amplifier formed by differential amplifier 90 and resistor 70. The voltage across the resistor can be converted to a digital value by an ADC 80. Gain may be applied by an intermediate amplifier 430.

The ADC may be a differential ADC as shown, or it may be single ended since the voltage at the inverting input of the amplifier should be stable and known as it should match the voltage at the non-inverting input which in turn is related to $V_{REF1}$.

Figure 11:
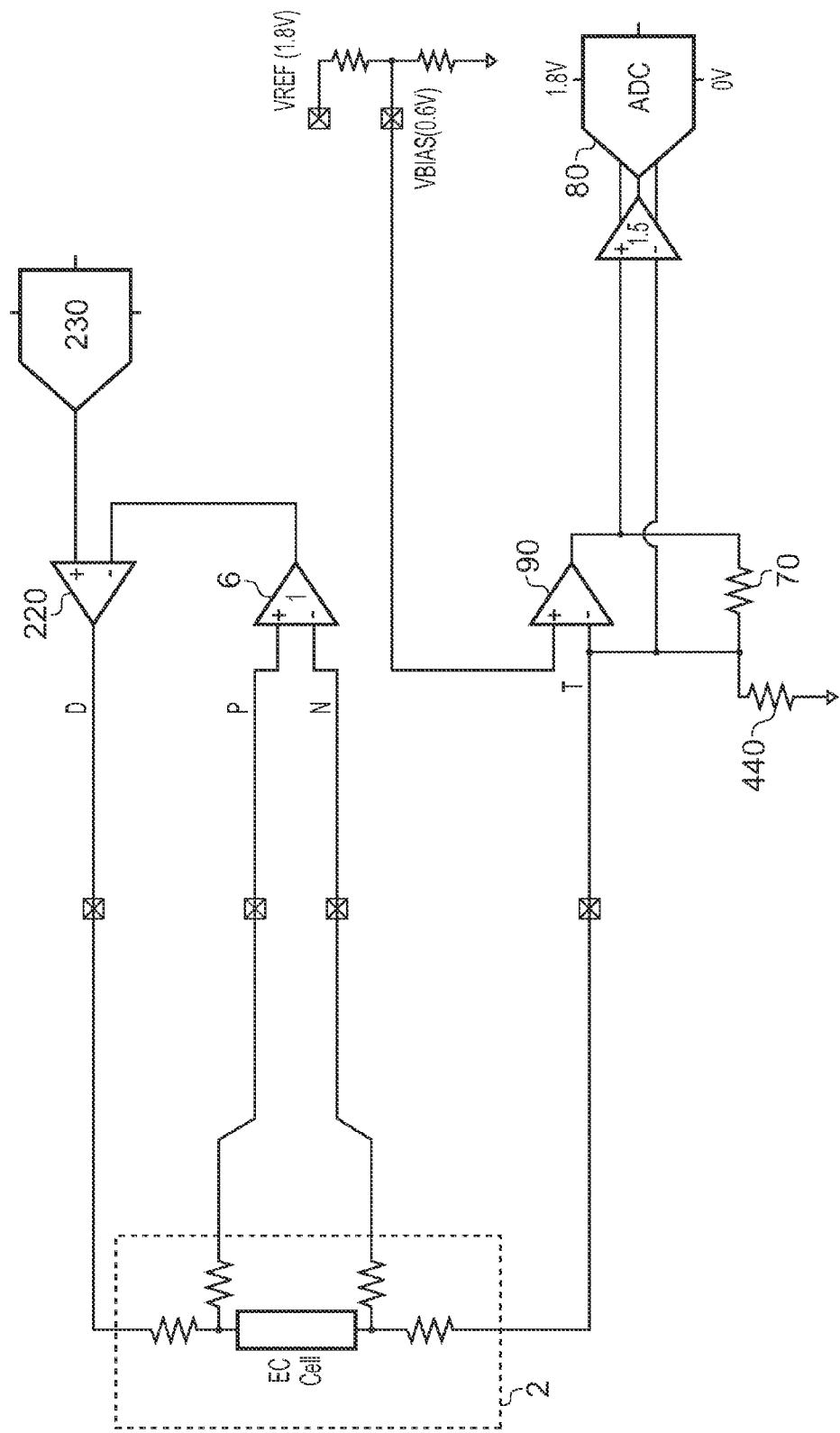
FIG. 11 is a schematic diagram of a modification allowing increased current measurement sensitivity for an electrochemical cell energized with a unipolar drive signal.

The transconductance amplifier may be modified as shown in FIG. 11. The circuit of FIG. 11 circuit omits the attenuators (although they could have been included) and allows increased current measurement resolution to be achieved. A further resistor 440 is connected between a low impedance node, such as one of the 0V or negative supply rail and the inverting input of the amplifier 90. This forms a gain stage configuration around the operational amplifier 90.

Figure 12:
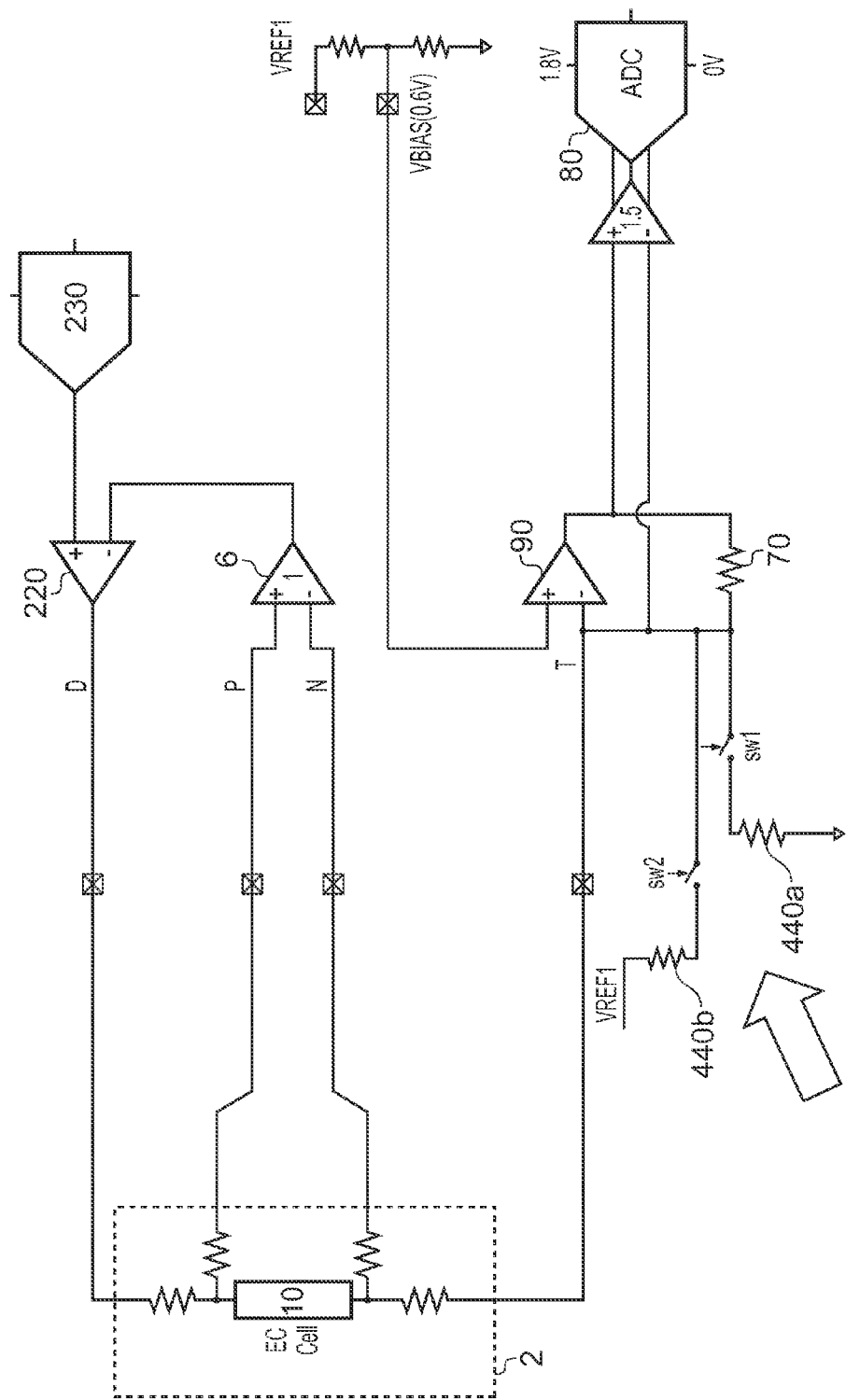
FIG. 12 is a schematic diagram of a modification allowing increased current measurement sensitivity for an electrochemical cell energized with a bipolar drive signal.

A similar technique can be adopted when the excitation signal is bipolar. However now the additional resistance needs to be alternately connected to $V_{REF1}$ or to ground depending on the polarity of the excitation signal. A circuit for doing this is shown in FIG. 12 where the resistor 440 has been replaced by resistors 440a and 440b in association with respective switches SW1 and SW2. Resistor 440a and switch SW1 can be used to connect the inverting input of amplifier 90 to ground, whereas resistor 440b and switch SW2 can be used to connect the inverting input to $V_{REF1}$ or some other voltage as appropriate. The switches are operated in antiphase.

It is thus possible to provide level shifters, attenuators and drive circuits to scale and shift an input voltage into a suitable operating range to allow a processing circuit to cope with a wider range of input voltages.

The claims presented here are written in single dependent format so as to be suitable for filing at the USPTO. However, for use in other jurisdictions where multiple dependent claims are frequently used, each dependent claim is to be assumed to be multiply dependent on all preceding dependent claims sharing the same independent claim, except where this is clearly not technically feasible.

The invention claimed is:

1. A control circuit for use with a sensor, the control circuit comprising:
   first and second drive terminals;
   first and second measurement terminals;
   wherein the control circuit is configured to drive at least one of the first and second drive terminals with an excitation signal, and to control the excitation signal such that a voltage difference between the first and second measurement terminals is within a target range of voltages; and
   wherein the control circuit further comprises a voltage level shifter between a measurement terminal of the first and second measurement terminals and a transistor control node of an amplifier, the voltage level shifter configured to adjust a voltage received from the corresponding measurement terminal and to provide a stable bias of the transistor control node of the amplifier within an input common mode operating range of the amplifier.

2. The control circuit of claim 1, wherein the voltage level shifter includes an attenuator configured to attenuate the voltage received from the corresponding measurement terminal.

3. The control circuit of claim 2, wherein the attenuator is configured to apply an offset to the voltage received from the corresponding measurement terminal.

4. The control circuit of claim 2, wherein an attenuation factor of the attenuator is adjustable.

5. The control circuit of claim 1, including a driver circuit, the driver circuit receiving a different supply voltage from a controller.

6. The control circuit of claim 1, including a driver circuit arranged to receive a first offset voltage, and to add the first offset voltage to the excitation signal.

7. The control circuit of claim 6, in which the first offset voltage is adjustable.

8. The control circuit of claim 1, comprising a current measuring circuit configured to receive the current through the sensor and a second offset voltage, and to urge the second drive terminal of the sensor towards the second offset voltage.

9. The control circuit of claim 8, comprising a phase detector for detecting a phase difference between voltage at the sensor and current flow through the sensor.

10. The control circuit of claim 8, wherein the current sensor includes a second amplifier in a virtual earth configuration, and wherein the second amplifier is configured to receive the second offset voltage at a non-inverting input.

11. The control circuit of claim 10, including a resistance connected between an inverting input of the second amplifier and a further voltage.

12. The control circuit of claim 11, wherein the further voltage is a local 0V supply.

13. The control circuit of claim 11, wherein the further voltage is adjustable between first and second voltages as a function of a polarity of the drive signal.

14. The control circuit of claim 1, in combination with a four terminal sensor having an impedance that changes in response to a measurand, where the measurand is a biological sample, or the measurand is blood glucose level.

15. The control circuit of claim 1, in combination with a four terminal sensor for measuring parameters of biological samples, where a plurality of impedance measurements are made at a plurality of frequencies so as to determine correction factors for use in a measurement of a biological parameter.

16. The control circuit of claim 1, including a controller, the controller including the amplifier, wherein the controller is configured to receive one or more level-shifted voltages from the means for voltage level shifting.

17. The control circuit of claim 16, including a driver circuit configured to receive a first offset voltage and an output of the controller, and to provide the excitation signal.

18. The control circuit of claim 17, wherein a supply voltage of the driver is higher than a supply voltage of the controller.

19. The control circuit of claim 17, including a digital-to-analog converter configured to provide the first offset voltage.

20. A control circuit for use with a sensor, the control circuit comprising:
   first and second drive terminals;
   first and second measurement terminals;
   wherein the control circuit is configured to drive at least one of the first and second drive terminals with an excitation signal, and to control the excitation signal such that a voltage difference between the first and second measurement terminals is within a target range of voltages; and wherein the control circuit further comprises means for voltage level shifting between a measurement terminal of the first and second measurement terminals and a transistor control node of an amplifier, the means for voltage level shifting configured to adjust a voltage received from the corresponding measurement terminal and to provide a stable bias of the transistor control node of the amplifier within an input common mode operating range of the amplifier.

\* \* \* \* \*